United States Patent [19]

Salerno

[11] Patent Number: 4,953,559
[45] Date of Patent: Sep. 4, 1990

[54] CATHETER FOR ENDOCARDIAL BIOPSY, WHICH CAN ALSO BE USED FOR IDENTIFYING THE POINT OF ORIGIN OF VENTRICULAR ARRHYTHMIA

[75] Inventor: Jorge A. Salerno, Pavia, Italy

[73] Assignee: Consiglio Nazionale Delle Ricerche, Rome, Italy

[21] Appl. No.: 270,582

[22] Filed: Nov. 14, 1988

[30] Foreign Application Priority Data

Nov. 16, 1987 [IT] Italy ............................... 67978 A/87

[51] Int. Cl.⁵ ............................................. A61B 10/00
[52] U.S. Cl. ..................................... 128/751; 606/39; 606/40
[58] Field of Search ...................... 128/303.13–303.17, 128/321, 642, 749, 751; 606/32, 34, 37, 39, 40

[56] References Cited

U.S. PATENT DOCUMENTS 3,964,468  6/1976  Schulz ................................. 128/751
4,184,486  1/1980  Papa ..................................... 128/642

FOREIGN PATENT DOCUMENTS 2310137  1/1977  France ............................. 128/303.17
575103  10/1977  U.S.S.R. ......................... 128/303.14

Primary Examiner—Randall L. Green
Assistant Examiner—Randy Shay
Attorney, Agent, or Firm—Sughrue, Mion, Zinn, Macpeak & Seas

[57] ABSTRACT

A catheter for endocardial biopsy comprises a distal portion provided with biopsy forceps including two jaws which are movable relative to each other between an open position and a closed position, and means which are operable from the proximal end of the catheter for causing the movement of the jaws. The two jaws of the forceps are of electrically conductive material, are insulated from each other, and are connected respectively to two terminals situated at the proximal end of the catheter so that, when the jaws are in their open position, they can be used as electrodes for identifying the point of origin of a ventricular arrhythmia. It is thus possible to carry out an endocardial biopsy in apparently normal patients with ventricular arrhythmia, tissue samples being taken both in correspondence with the zone of origin of the arrhythmia and in correspondence with other zones, immediately after the identification of the zone of origin. In a variant, one of the two electrodes is constituted by the two jaws and the other by a ring carried by the body of the catheter and arranged coaxially with the catheter.

4 Claims, 2 Drawing Sheets

CATHETER FOR ENDOCARDIAL BIOPSY, WHICH CAN ALSO BE USED FOR IDENTIFYING THE POINT OF ORIGIN OF VENTRICULAR ARRHYTHMIA

BACKGROUND OF THE INVENTION

The present invention relates to catheters for endocardial biopsy.

The term "biopsy" generally means the removal of a fragment of living tissue for diagnostic purposes. An endocardial biopsy is currently carried out in cases of suspected myocarditis or cardiomyopathy. According to conventional techniques, the biopsy is carried out by means of a catheter the distal end of which carries sampling forceps. This distal end is made to enter the heart through a blood vessel under X-ray or echographical control. Currently, an endocardial biopsy is performed on patients who already have obvious signs of myocarditis or cardiomyopathy, in order to confirm the diagnosis. It would be desirable, however, to be able to use endocardial biopsy for the timely identification of the existence of a cardiomyopathy or myocarditis when the patient does not yet have obvious signs. There are, for example, apparently healthy patients in whom ventricular arrhythmia in turn precedes the manifestation of obvious signs of myocarditis or cardiomyopathy. In these cases, an endocardial biopsy could enable early diagnosis, provided that it were possible to take tissue samples with certainty, both in correspondence the zone of origin of the arrhythmia and in correspondence with zones remote therefrom. It would therefore be necessary to be able precisely to identify the point of origin of the arrhythmia immediately before the sampling is carried out at that point.

Catheters of various types are already known (see, for example, U.S. Pat. No. 4,649,924, assigned to the same Applicant) which are provided with electrodes that can detect the electrical potential at various points on the heart wall, so as to enable the point of origin of the arrhythmia to be identified. In theory, therefore, it should be possible to insert firstly a catheter of this type for the detection of the origin of the arrhythmia and secondly the catheter for the biopsy. However, this manner of operation has the disadvantage that it takes a very long time, with adverse consequences for the patient, and is in any case not very reliable since it is difficult to ensure that the tissue sampling is carried out exactly in correspondence with the zone identified as the origin of the arrhythmia.

SUMMARY OF THE INVENTION

The object of the present invention is to resolve the problem specified above.

In order to achieve this object, the subject of the invention is a catheter for endocardial biopsy of the type indicated at the beginning of the present description, characterised in that, in correspondence with its distal portion, the catheter is provided with at least two electrodes—at least one of which is constituted by one of the two jaws of the biopsy forceps—which are connected electrically to two terminals situated at the proximal end of the catheter so that the latter can be used for identifying the point of origin of a ventricular arrhythmia. In accordance with conventional techniques used for electrical catheters, the two terminals are connected to an instrument for reading and recording the electrical signals from the heart. In a preferred embodiment, the two electrodes are constituted by the two jaws of the biopsy forceps, which are of electrically conductive material and are electrically insulated from each other when they are in the open position.

After insertion, the catheter according to the invention is used firstly with its jaws open to identify the origin of the ventricular arrhythmia. Once this operation has been carried out, the catheter can be used to take a tissue sample in correspondence with the zone identified. Tissue samples can be taken both in correspondence with the point or origin of the arrhythmia and in correspondence with other zones, so as to enable a comparison between the various samples taken and the identification of any degenerative phenomena premonitory of cardiomyopathy or myocarditis. The biopsy thus enables the disease to be diagnosed long before the time when it gives rise to obvious signs. Experiments carried out by the inventor have successfully shown the advantages of the invention. In some cases, he was able to diagnose myocardial abnormality in apparently healthy patients who were, however, exhibiting ventricular arrhythmia. In some of the patients, the degenerative abnormalities were identified only in correspondence with the zone of origin of the arrhythmia, which shows that the performance of a biopsy without the prior identification of the zone of origin may lead to the degeneration not being identified.

BRIEF DESCRIPTION OF THE DRAWINGS

Further characteristics and advantages of the invention will become clear from the description which follows with reference to the appended drawings, provided by way of non-limiting example, in which.

DETAILED DESCRIPTION OF THE INVENTION

Figure 1:
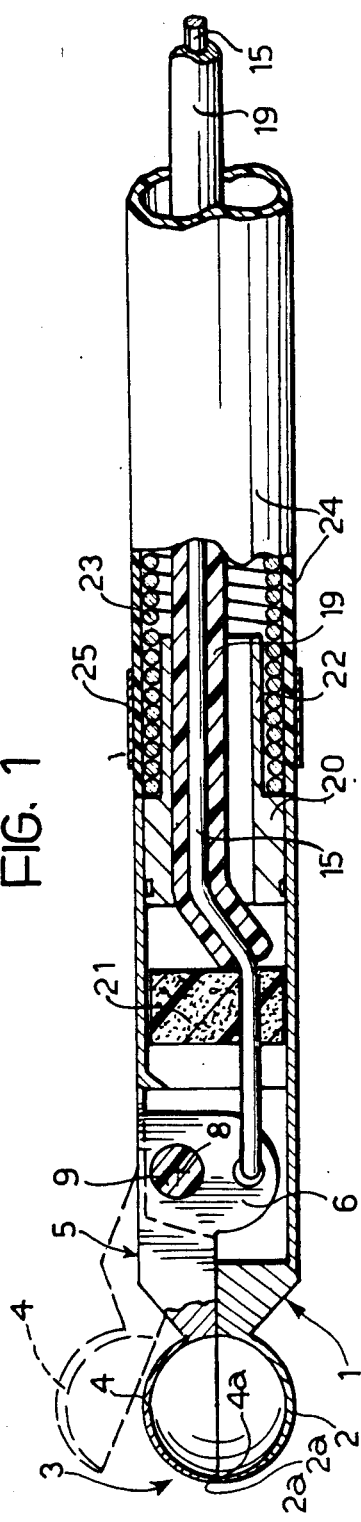
FIG. 1 is a section of the distal end of the catheter according to the invention, on an enlarged scale.
Figure 2:
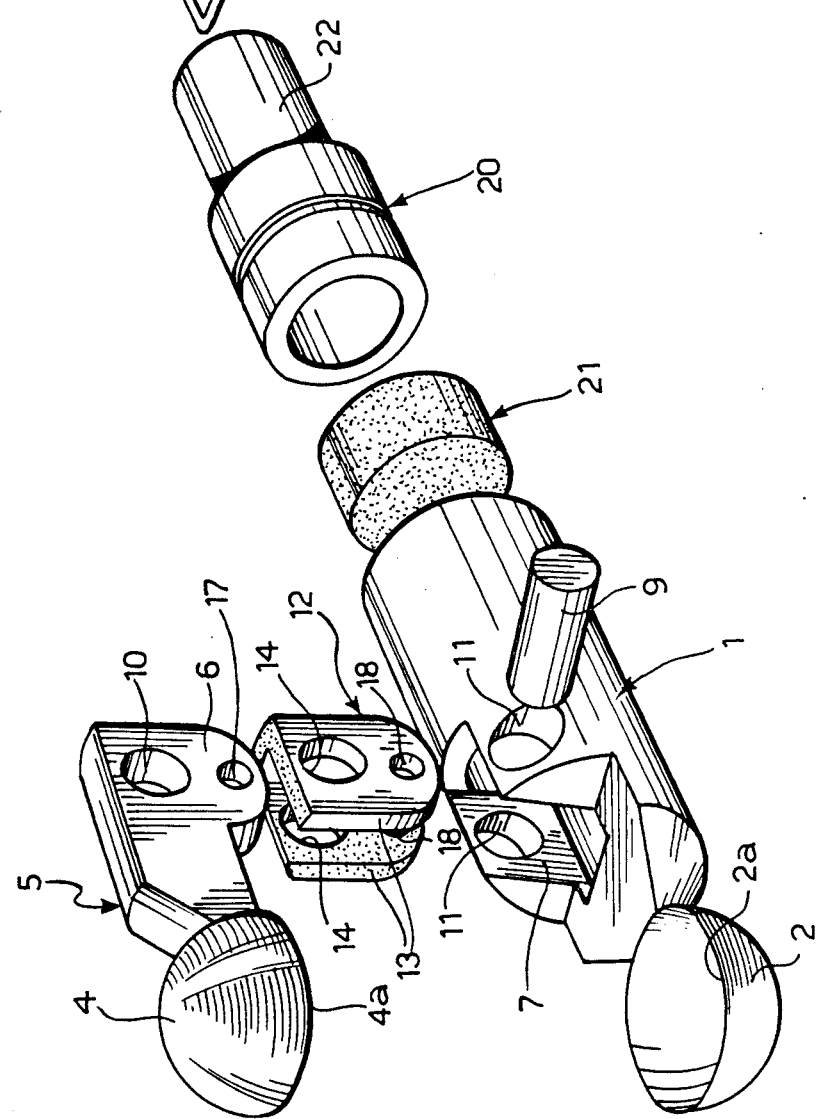
FIG. 2 is an exploded perspective view of the part illustrated in FIG. 1.

With reference to FIGS. 1 and 2, the catheter according to the invention includes, at its distal end, a substantially tubular body 1 which terminates at one end in a spoon-like appendage 2 constituting one of the jaws of a pair biopsy forceps 3. The spoon-like appendage 2 has a free cutting edge 2a which extends through approximately 320°. The other jaw of the forceps is constituted by a spoon-like appendage 4 which is similar in shape to the spoon-like appendage 2 and has its cavity facing that of the appendage 2. The appendage 4 also has a circumferential free cutting edge 4a which cooperates with the edge 2a to effect the removal of the heart tissue. The appendage 4 is carried by a support lever 5 which has a flat part 6 housed in a transverse notch 7 formed in the supporting body 1. The lever 5 is articulated to the supporting body 1 about a transverse axis 8 by means of an articulation pin 9. The pin 9 engages a hole 10 formed in the flat part 6 of the support lever 5 and two holes 11 formed in the two walls of the supporting body 1 which define the transverse notch 7.

The supporting body 1 incorporating the jaw 2 and the lever incorporating the jaw 4 are both made of an electrically conductive material, preferably biocompatible stainless steel. These two bodies are electrically insulated from each other, however, by virtue of the fact that the articulation pin 9 is made from an electrically insulating material, for example, the material marketed under the trade mark "Delrin" by Du Pont de Nemours GmbH. Moreover, a body 12 of insulating material, for example, the same material as forms the pin 9, is interposed between the lever 5 and the sides of the transverse notch 7. The body 12 is U-shaped with two parallel flanges 13 which have facing holes 14 for the engagement of the articulation pin 9. The flanges 13 are interposed between the two sides of the lever 5 and the surfaces of the transverse notch 7 which face them.

The lever 5 is therefore able to rotate about the axis 8 relative to the supporting body 1 so as to move the jaw 4 between a closed position (shown in continuous outline in FIG. 1) and an open position (illustrated in broken outline). In the closed position, the two cutting edges 2a, 4a meet each other and the two spoon-like appendages define a closed cavity for containing the tissue sample taken. The jaw 4 can be moved between the closed position and the open position from the proximal end of the catheter (in the manner which will be described in more detail below) by means of a rigid metal cable 15, for example of stainless steel, which runs along the whole length of the catheter and ends in an eyelet 16 at the distal end of the catheter. This eyelet part engages an additional hole 17 formed in the flat part 6 of the lever 5 and two corresponding holes 18 formed in the sides 13 of the insulating body 12. The operating cable 15 is electrically insulated by a covering 19 of insulating material, for example, polyurethane or polytetrafluoroethylene (teflon).

A cylindrical body 20 of electrically conductive material, for example, stainless steel, is inserted with interference in the open end of the supporting body 1. A cylindrical body 21 of closed-cell foam material (for example, polyurethane or teflon) is situated in the section of the internal cavity of the supporting body 1 between the body 20 and the articulation of the lever 5 to prevent the escape of blood. The metal cable 15 passes through the foam body 21 and is fast therewith. The movement of the cable 15 therefore causes the foam body 21 to slide correspondingly within the supporting body 1.

The body 20 has an axial appendage 22 of reduced diameter, onto which one end of a helical metal spiral 23 running the whole length of the catheter is fitted. The spiral 23, like all the other metal components of the catheter, is preferably made of stainless steel, for example, inox 404 steel or another similar biocompatible alloy. The spiral 23 is insulated from the metal cable 15 by virtue of the covering thereof and is also insulated externally by means of a flexible sheath 24 which runs along the whole length of the catheter and is made, for example, from polyurethane or teflon. An external clip 25 is provided in correspondence with the appendage 22 for clamping the sheath 24 and the spiral 23 to the appendage. The spiral 23 is thus connected electrically to the jaw 2 by means of the supporting body 1 and the body 20, whilst the other jaw 4 is connected electrically to the metal cable 15.

As already indicated above, the outer sheath 24, the spiral 23 and the metal cable 15 with its covering 19 run along the whole length of the catheter. At the proximal end of the catheter, the spiral 23 is fitted onto an appendage 25 of a tubular metal body 26. The latter is connected at its opposite end to a support body 27, also of metal, which is tubular in shape and on which a rigid sleeve 28 of insulating material, for example Delrin, is slidably mounted. The spiral 23 is clamped to the appendage 25 by means of a clip 29 which surrounds the outer sheath 24. A terminal pin 30 is also fixed to the body 26 and is thus connected electrically to the jaw 2 through the body 26, the spiral 23, the body 20 and the body 1. The sleeve 28 is provided with a terminal pin 31 which passes through a slot 32 formed in the support body 27 and is connected to the proximal end of the metal cable 15, which is formed as an eyelet. The terminal pin 31 is therefore connected electrically to the jaw 4 by means of the cable 15 and the lever 5.

Figure 3:
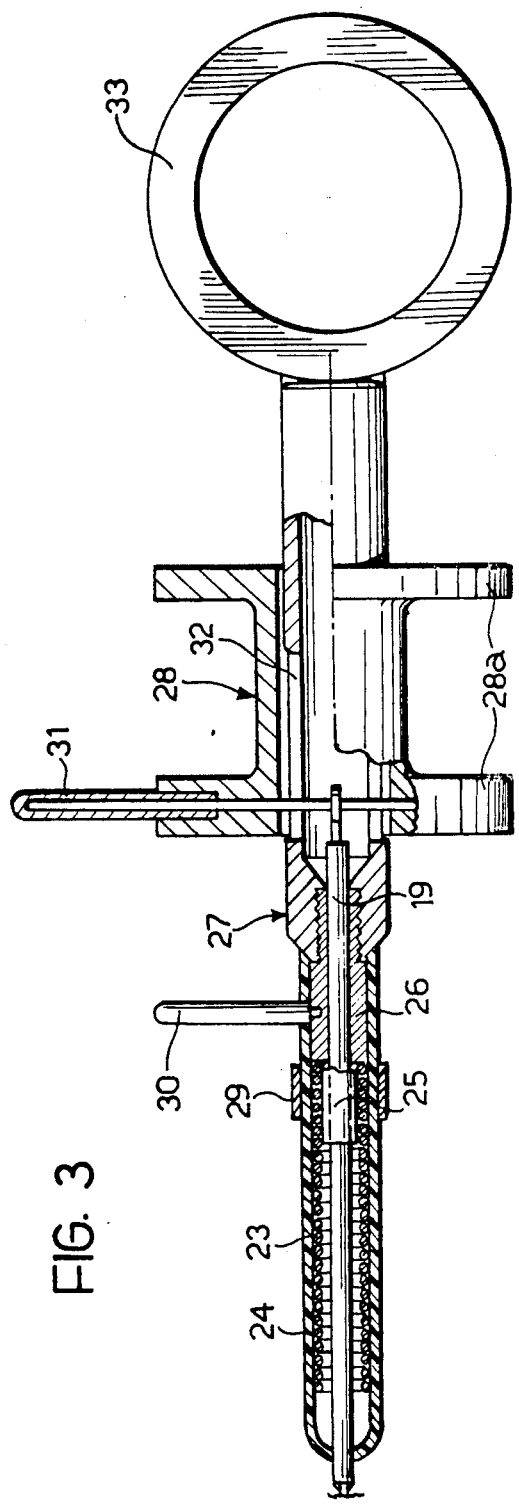
FIG. 3 is a section of the proximal end of the catheter according to the invention, on an enlarged scale.

The support body 27 is provided with a ring 33 at its end. The catheter is operated by gripping its proximal end with one hand, the thumb being inserted in the ring 33 and one or two fingers being placed between the end flanges 28a of the sleeve 28. In the position shown in FIG. 3, the sleeve 28 is in its forwardmost position which corresponds to the opening of the forceps 3. In order to close the forceps, the sleeve 28 must be moved back towards the ring 33.

In one embodiment, the outer diameter of the catheter is 2.3 mm. Its length is preferably between 90 and 120 cm.

In a variant, the distal end portion of the catheter has a curvature of 90°–120°, 3.5–5 cm from the tip. According to the conventional techniques, the catheter is inserted into the heart cavity through a blood vessel, it being passed through a tubular sheath inserted beforehand.

When the forceps 3 have reached a ventricle, they can be used, in their open condition, as a dipole for detecting the electrical heart signals. The terminal pins 30 and 31 are connected to an electrical instrument for reading and recording the signals detected. The two electrodes constituted by the jaws 2, 4 thus enable a map of the electrical potential along the heart wall to be produced and the point with the absolute maximum potential, which corresponds to the point of origin of the ventricular arrhythmia, consequently to be identified. Once the zone origin of the ventricular arrhythmia has been identified, the catheter can immediately be used as a biotome. The sleeve 28 is moved to cause the closure of the forceps which thus remove a tissue sample in the zone identified. It is thus possible to effect both the identification of the zone of origin of the ventricular arrhythmia and the removal of tissue samples with the same catheter. As already indicated above, the removal is preferably carried both in the zone of origin of the ventricular arrhythmia and in other zones. During the search for the zone of origin, a detailed map of the electrical potential on the heart wall can be produced by virtue of the fact that the separation of the two electrodes, that is, the distance between the two jaws in the open condition of the forceps, is quite small (approximately 3 mm in one embodiment).

Naturally, flexible electrical cables could be used in place of the terminal pins 30, 31. Moreover, the catheter is preferably surrounded by a sheath (not illustrated) in the region of the pin 9, to avoid the risk of the latter coming out of its seat.

Figure 4:
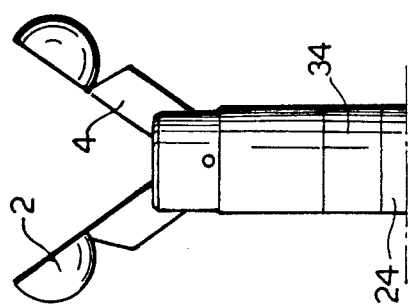
FIG. 4 is a schematic view of the distal end according to a possible variant.

Furthermore, the details of construction and forms of embodiment may of course be varied widely with respect to those described and illustrated purely by way of example, without thereby departing from the scope of the present invention. FIG. 4 shows a variant in which both the jaws 2, 4 are movable. In this case, one of the two electrodes is constituted jointly by the two jaws when they are closed, whilst the second electrode is constituted by a metal ring 34 mounted on the insulating sheath of the catheter. In this case, the electrodes are arranged coaxially with the catheter.

What is claimed is:

1. A catheter for cardial biopsy, including distal and proximal end portions, biopsy forceps provided at the distal end and including two jaws which are movable relative to each other between an open position and a closed position, and means which are operable from the proximal end of the catheter for moving the jaws, wherein at least two electrodes are provided in correspondence with the distal portion, said electrodes being constituted by the two jaws of the forceps, with said jaws being made from electrically conductive material and being electrically insulated from each other in their open position, wherein two terminals are situated at the proximal end of the catheter and are connected electrically to the electrodes so that the catheter can be used for identifying the point of origin of a ventricular arrhythmia, wherein the distal end of the catheter has a supporting body which incorporates one jaw of the forceps, and wherein the catheter also includes a lever which forms the other jaw and a pin of insulating material by means of which the lever is articulated to the supporting body, and wherein the catheter includes a helical metal spiral which runs along the whole length of the catheter, one end of the spiral being connected to the supporting body and an opposite end of the spiral being connected to one of the terminals.

2. A catheter according to claim 1, wherein a rigid metal operating cable runs along the whole length of the catheter within the metal spiral and is provided with an insulating sheath, the distal end of the cable being connected to the lever and its proximal end being connected to the other terminal.

3. A catheter according to claim 1, wherein the supporting body defines a transverse notch and the lever defining one of the jaws of the forceps has a flat part housed in the said notch, and wherein the catheter further includes a U-shaped body of insulating material having two flanges which are interposed between the two sides of the flat part and the surfaces of the notch which face them, the flanges defining facing holes for the engagement of the pin.

4. A catheter according to claim 2, wherein the proximal end of the catheter has a support body which defines a slot and is connected electrically to the metal spiral, and a sleeve of insulating material is slidable mounted on the support body, the sleeve being provided with a terminal pin of electrically conductive material which passes through the slot formed in the support body and is connected to the proximal end of the metal operating cable.

* * * * *